United States Patent [19]

Hartigan, Jr.

[11] Patent Number: 5,396,904
[45] Date of Patent: Mar. 14, 1995

[54] APPARATUS FOR CONTAINING AND COLLECTING DEBRIS GENERATED DURING MEDICAL PROCEDURES

[76] Inventor: William J. Hartigan, Jr., 10 Indian Rock Dr., Saugus, Mass. 01906

[21] Appl. No.: 125,067

[22] Filed: Sep. 21, 1993

[51] Int. Cl.⁶ ............................................. A61B 19/00
[52] U.S. Cl. ...................................... 128/849; 128/853
[58] Field of Search ....................... 128/853, 849, 850; 600/21

[56] References Cited

U.S. PATENT DOCUMENTS

| | | | |
|---|---|---|---|
| 2,473,033 | 6/1949 | Letac . | |
| 3,000,379 | 9/1961 | Viers . | |
| 3,450,450 | 6/1969 | Hopkins et al. . | |
| 3,678,921 | 7/1972 | Brendgord et al. . | |
| 3,850,172 | 11/1974 | Cazalis . | |
| 4,224,935 | 9/1980 | Metelnick . | |
| 4,275,719 | 6/1981 | Mayer . | |
| 4,335,712 | 6/1982 | Trexler | 600/21 |
| 4,346,699 | 8/1982 | Little et al. . | |
| 4,366,809 | 1/1983 | Trexler . | |
| 4,562,834 | 1/1986 | Bates et al. . | |
| 4,596,245 | 6/1986 | Morris . | |
| 4,691,695 | 9/1987 | Birk et al. . | |
| 4,727,864 | 3/1988 | Wiesenthal et al. . | |
| 4,745,915 | 5/1988 | Enright et al. . | |
| 4,865,049 | 9/1989 | Gatti . | |
| 4,903,710 | 2/1990 | Jessamine et al. | 128/849 |
| 4,926,882 | 5/1990 | Lawrence | 128/853 X |
| 4,936,318 | 6/1990 | Schoolman | 128/849 X |
| 4,974,604 | 12/1990 | Morris | 128/853 |
| 4,998,538 | 3/1991 | Charowsky et al. . | |
| 5,020,546 | 6/1991 | Russo | 128/849 |
| 5,027,832 | 7/1991 | Williams, Jr. | 128/849 |
| 5,063,919 | 11/1991 | Silverberg . | |
| 5,074,316 | 12/1991 | Dowdy . | |
| 5,083,557 | 1/1992 | Lennon et al. . | |

FOREIGN PATENT DOCUMENTS

| | | | |
|---|---|---|---|
| 851240 | 7/1952 | Germany | 600/21 |

*Primary Examiner*—Steven A. Bratlie
*Attorney, Agent, or Firm*—Patterson & Keough

[57] ABSTRACT

A containment device for use by a medical practitioner during medical procedures on a portion of a patient. The containment device is comprised of a transparent, disposable receptacle for substantially enclosing a portion of the patient. The receptacle has a first end opening defined by a lip. A first aperture is for receiving the portion of the patient and a closed second end to substantially envelope the portion of the patient and to contain the debris generated during a medical procedure. At least one second aperture is for providing access of the medical practitioner to treat the patient within the containment device. A resilient, transparent viewing member is adapted to support the receptacle. An attachment mechanism is included for detachably attaching the first end lip of the receptacle to the viewing member such that the receptacle depends beneath the viewing member. A frame is adapted to support the receptacle and the viewing member.

7 Claims, 5 Drawing Sheets

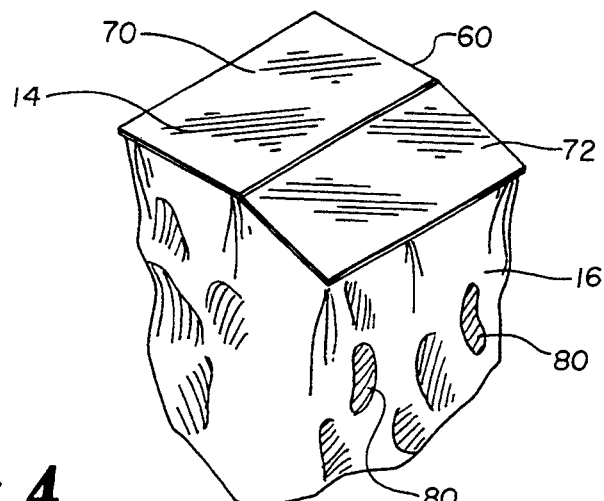
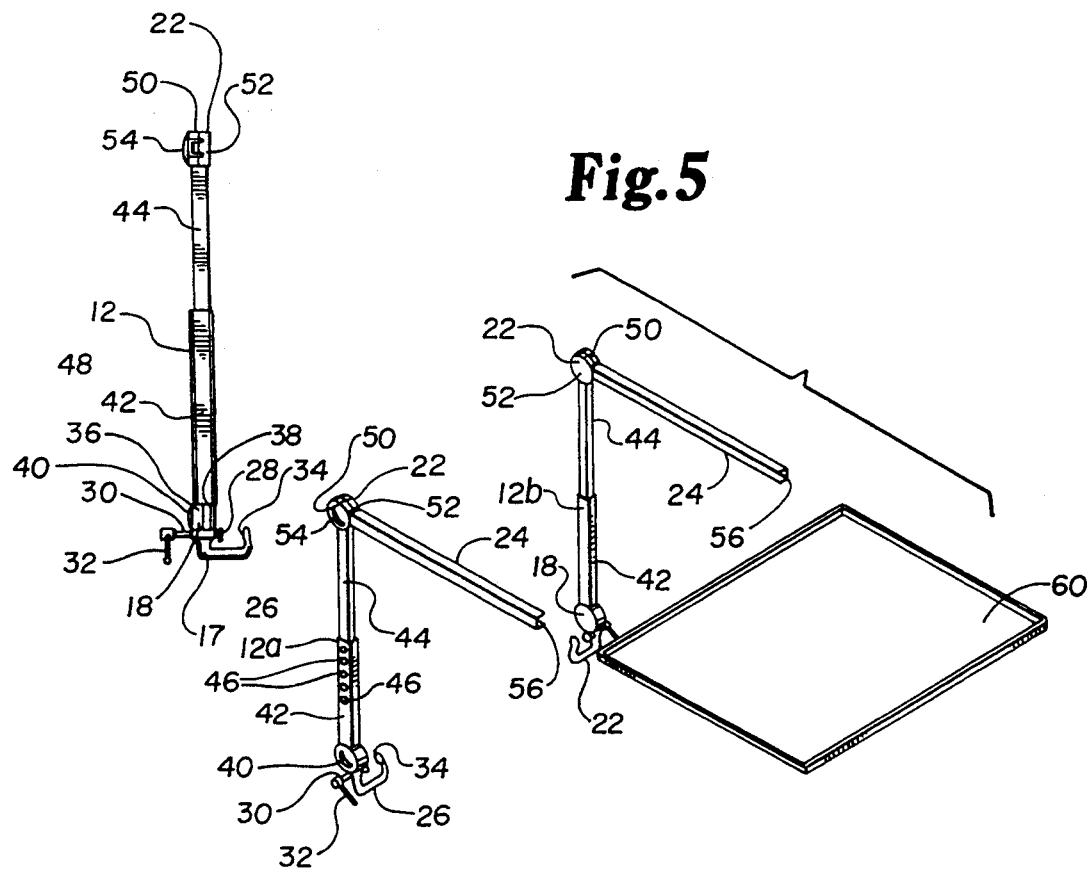

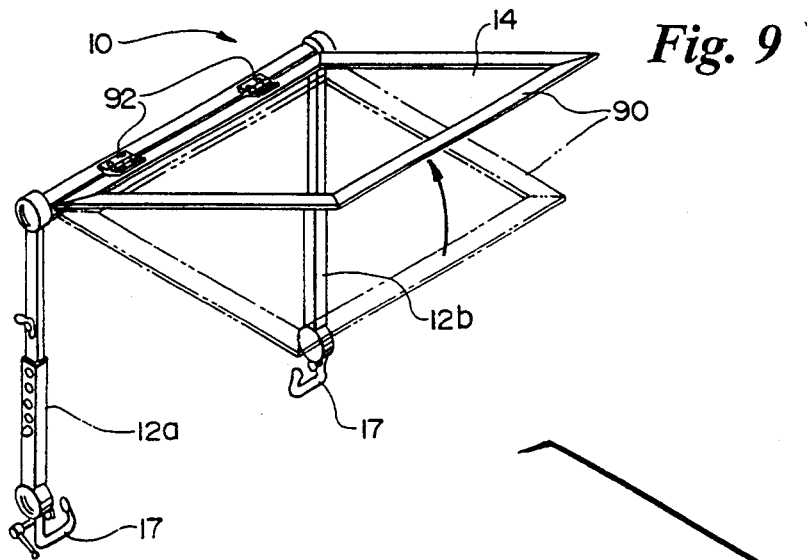
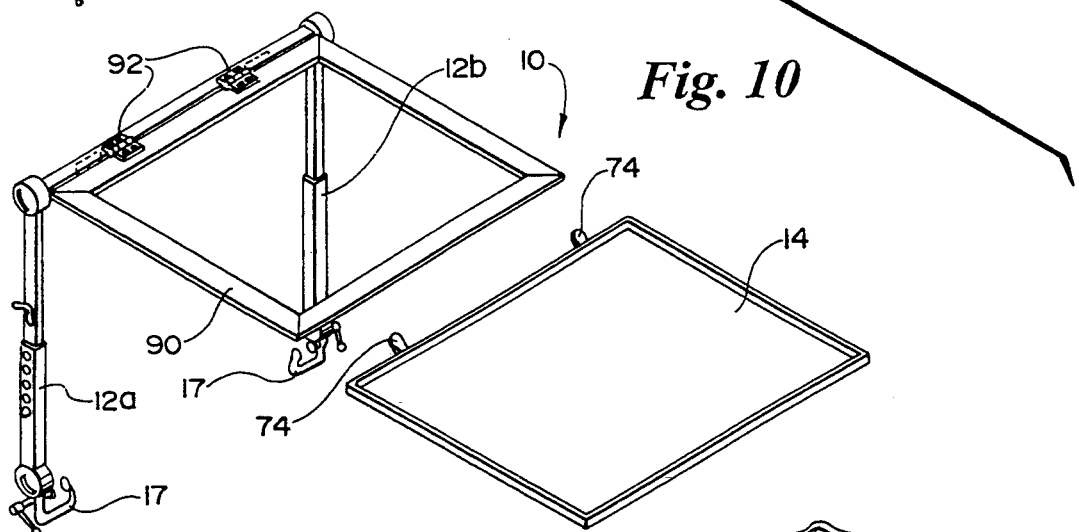
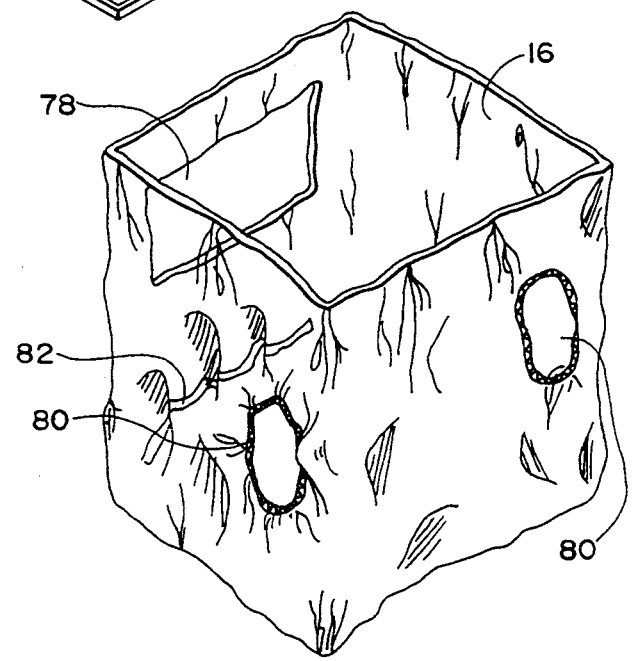

APPARATUS FOR CONTAINING AND COLLECTING DEBRIS GENERATED DURING MEDICAL PROCEDURES

TECHNICAL FIELD

The present invention relates to devices for reducing or preventing the discharge of harmful biological substances from an area isolated by the device to the surrounding environment and for the ready containment and removal of such substances. In particular, it relates to a transparent container that is placed for envelopment of a portion of a human patient on which a medical procedure is to be performed so as to contain residue at the site of the procedure and for removal and disposal of such residue.

BACKGROUND OF THE INVENTION

There is a need in the medical field today for simple, expendable means to collect and convey debris generated during medical procedures from the office or room in which the procedure is performed for proper disposal of such debris. Such materials as must be contained and removed result from the use of cutting devices such as drills, cleaning picks, reamers, saws, and similar devices, and may comprise toenail dust, bone dust, clippings, and skin particles. Additionally, a need exists to minimize the exposure of medical personnel and subsequent patients to any contaminated airborne material that is produced during medical procedures on a patient. This requires a device that contains the bulk of the debris that is generated during a medical procedure, yet presents minimal interference to the medical practitioner's ability to perform the procedure. The device should additionally provide for the ready removal and disposal of the debris and be adapted for the ready cleaning of the device in preparation for the next patient. The device should perform these functions without the need to resort to the complexity of air exchange and filtration systems.

The best approach to the problem of containing residue of medical procedures is to provide containment of the contaminated material at its source, as opposed to removing it once it has passed into the procedure room environment or by requiring additional protective clothing to be worn by the medical personnel. A device affording this type of containment should permit the medical personnel to view the portion of the patient on whom the procedure is being performed while the device is in place. The device should permit the medical personnel to have their hands in close contact with the patient with minimum release of potentially contaminated material. Further, such a device should be inexpensive, disposable, and easy to use and clean.

In the past, numerous devices have been proposed that focus on the need to provide a barrier between the patient and the medical personnel. However very little thought has been given to the problem of containment and removal of the debris, which is as much a part of the sanitation problem as providing the barrier. Consequently, as will be seen in reviewing the prior art, the past devices do not include structure that is adapted for the ultimate containment and removal of debris generated during a medical procedure in addition to providing a barrier while the procedure is being performed.

U.S. Pat. No. 4,865,049 discloses a vacuum barrier specific for electrocautery surgery. It relies on a vacuum to capture the smoke generated during the procedure. It includes no device for capturing and disposing of heavier or larger particles. This device is mounted directly on the patient and thus requires an adhesive, which a significant number of people may be allergic to.

U.S. Pat. No. 4,936,318 discloses a transparent shield with means to draw a vacuum around the periphery of the shield. The shield is positioned over the recumbent patient. The device relies on the vacuum system to protect the environment outside of the shield from aerosol material that rises from the patient. Vacuums can fail to contain heavier particles, such as toenails. Vacuum units additionally have major limitations regarding portability, expense, cleaning and mechanical failure. The device offers no method of collecting debris that the vacuum fails to capture. The device is basically a single unit and would either need to be entirely covered with a disposable barrier itself or require extensive cleaning between procedures.

U.S. Pat. No. 4,998,538 discloses a medical drape specifically designed for laser surgery. As with the device discussed above, its usefulness also relies heavily on a vacuum unit and is burdened with the same limitations previously mentioned. The device relies on the walls of the drape wrapping onto the laser to be suspended therefrom. The materials used to make the barrier are strictly limited by laser safety precautions i.e., moisture-absorbent and nonflammable. The laser is directed perpendicular to the tissue to being operated on. The enclosed nature of the barrier would make procedures of even moderate length unacceptable without some sort of air transfer system. No provisions are included to remove any of the debris that is generated by the medical procedure after completion of the procedure.

U.S. Pat. No. 4,275,719 discloses an apparatus and method for providing aseptic surgical environment. This apparatus is a complex system requiring various accessory machines, i.e., air recirculation and sterilization equipment. The internal bag is designed to adhere a portion of the body and isolate the patient's body from the site of operation. The external structure is rigid and does not adjust to assist the practitioner's viewing of the site of operation. It offers no means of debris collection and disposal.

It would be a decided advantage to have a containment device that encloses the portion of the patient being operated on, that is supported in position ready for use, that is readily positioned about the portion of the patient that is to be operated upon, that provides for ready viewing of the site of the medical procedure, that provides for ready access of the medical practitioner's hands to the site of the medical procedure, that is naturally ventilated, and provides a means to conveniently collect and remove debris generated during the medical procedure.

SUMMARY OF THE INVENTION

The needs recited above are in large measure solved by a debris containment and removal device made in accordance with the present invention. The containment device comprises an enveloping receptacle that substantially encloses the portion of the human patient on which the procedure is to be performed, a resilient transparent viewing portion through which the medical practitioner is able to clearly view the portion of the patient to be operated on and a frame that supports the enveloping receptacle and the viewing portion. The extremity of the patient on which the medical procedure is to be performed is preferably the lower portion of the leg, the ankle, and the foot.

The generally bag-shaped receptacle includes an open first end with attachment apparatus for adhering either to the frame or viewing portion and a substantially closed second end for enveloping the extremity during the medical procedure. An aperture is included in the receptacle through which the patient is able to insert his or her leg. Other apertures are included to admit the medical practitioner hands into the receptacle to perform the medical procedure.

The means by which the enclosure is attached to the frame or viewing portion is readily detachable to facilitate the removal of the receptacle from the patient after completion of the procedure. During the removal process the debris is retained in the bottom of receptacle. The receptacle may then be tied off or otherwise sealed and removed from the medical procedure room with the debris contained therein for proper disposal thereof.

The containment device in accordance with the present invention is preferably constructed of transparent polymeric film material such that the extremity may be readily viewed from outside the containment device when the extremity is enclosed within it. The containment device has a plurality of apertures passing through it for the insertion of the hands and forearms of the medical personnel through the device to perform palliative or like actions on the patient's extremity and for providing natural ventilation of the site of the medical procedure.

BRIEF DESCRIPTION OF DRAWINGS

FIG. 3 is a perspective of a second embodiment of the viewer depicting the viewer having a second, downwardly depending portion and the receptacle without the flap opening.

FIG. 4 is a frontal perspective of the support frame.

FIG. 5 is as perspective view of the two support frames and the viewer prior to insertion of the viewer into engagement with the support frames.

FIG. 9 is a perspective view of a hinged viewer frame that permits the viewer to be raised for cleaning after performing a medical procedure.

FIG. 10 is a perspective view of the hinged viewer frame as depicted in FIG. 9 and including a viewer that may be removed from the hinged frame and the removable receptacle.

DETAILED DESCRIPTION OF INVENTION

The containment device of the present invention as shown generally at 10. Several embodiments are depicted. Similar numbers are used in the depictions of the various embodiments to designate similar components of the invention. Containment device 10 consists of three major portions; frame 12, viewer 14, and receptacle 16.

Figure 1:
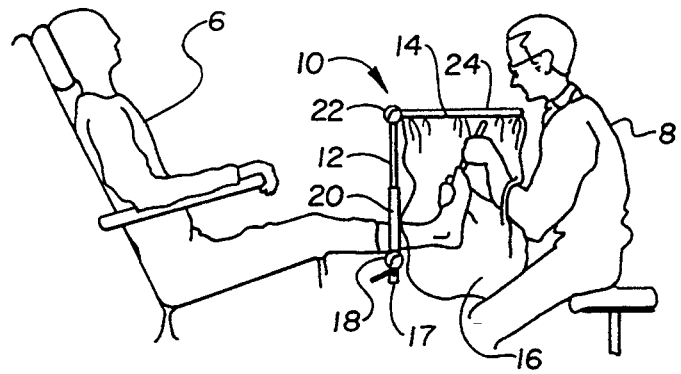
FIG. 1 is a side perspective of the invention used in conjunction with a podiatric treatment chair.
Figure 2:
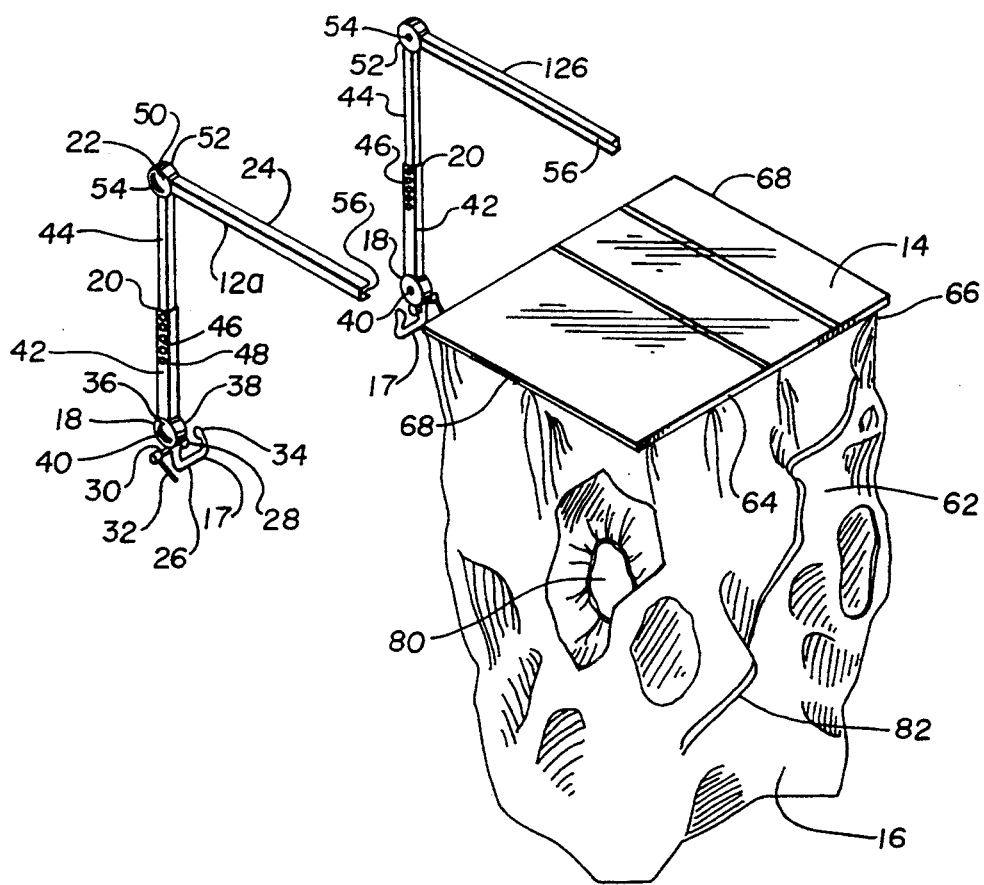
FIG. 2 is a perspective of the frame, the viewer and the receptacle of the invention prior to engagement of the viewer with the frame.

Referring to FIGS. 1 and 2, there are two cooperative frames 12, shown at 12a and 12b, that are of similar design and are oriented spaced apart from and facing one another. Frames 12a and 12b are designed to complement one another when in use. The following description pertains to both frames 12a, 12b.

Frame 12 has a first end that includes clamp 17. Clamp 17 is designed for easy attachment to the support upon which the patient is positioned. Clamp 17 is rotatably engaged to first rotatable joint 18. First rotatable joint 18 has an axis of rotation that is perpendicular to the axis of rotation of clamp 17. First rotatable joint 18 is affixed to a first end of first frame member 20. The second end of first frame member 20 is affixed to second rotatable joint 22. Second rotatable joint 22 connects first frame member 20 and second frame member 24.

In the preferred embodiment clamp 17 has a C clamp section 26, seen also in FIG. 4. The first end of C clamp 26 has a threaded bore that is not shown. Threaded shaft 30 is threaded into this bore. Threaded shaft 30 has a moveable head 28 and handle 32 for positioning threaded shaft 30 with respect to the threaded bore in the first end of C clamp section 26. The second end of C clamp section 26 consists of non-moveable head 34. Non-moveable head 34 and moveable head 28 oppose each other across C clamp section 26. First rotatable joint 18 has a base 36, that is affixed to clamp 17. Sleeve 38 is coaxial with base 36 and rotates therein. Butterfly nut 40 is coaxial with both base 36 and sleeve 38 and is capable of holding base 36 in a fixed position with respect to sleeve 38, as desired. Sleeve 38 is affixed to first frame member 20.

First frame member 20 has a first telescoping member 42. First telescoping member 42 substantially encloses second telescoping member 44. First telescoping member 42 and second telescoping member 44 are in sliding engagement with one another. A series of bores 46 are included in first telescoping member 42. A bore (not shown) is provided in second telescoping member 44 and may be aligned with any of the bores 46 in first telescoping member 42. Locking pin 48, best seen in FIG. 4, is provided to penetrate bore 46 and the aligned bore in second telescoping member 44 so that first telescoping member 42 and second telescoping member 44 are held in a desired fix position with respect to one another.

Second rotatable joint 22 is positioned at the second end of first frame member 20. Second rotatable joint 22 is similar in construction to first rotatable joint 18. Second rotatable joint 22 has a base 50 that is affixed to first frame member 20. Sleeve 52 is affixed to a first end of second frame member 24. Butterfly nut 54 is provided to fix the angular relationship of first frame member 20 and second frame member 24 by clamping down on base 50 and base 52.

In a preferred embodiment second frame member 24 has a channel 56 formed therein. Channel 56 of frame 12a and channel 56 of frame 12b are designed to oppose one another such that the opening portion of the channels 56 face one another.

A transparent viewer 14 extends between channel 56 of frame 12a and channel 56 of frame 12b and is held in place thereby. Transparent viewer 14 is formed of a resilient plastic material selected for its clear transparent qualities and its ability to endure repeated cleaning with antiseptic cleansers. In a preferred embodiment as depicted in FIGS. 2 and 5, viewer 14 has a first slidable portion 64 and a second slidable portion 66. First slidable portion 64 overlies second slidable portion 66. Translating portions 64, 66 with respect to one another adjusts the lateral dimension of transparent viewer 14. Lateral edges 68 of transparent viewer 14 are designed to be received within channel 56 of second frame members 24 on frames 12a, 12b.

An alternative embodiment of transparent viewer 14 is shown in FIG. 3. This embodiment shows a first portion 70 that is preferably generally held in a horizontal position. A second portion 72 is joined to first portion 70 at a depressed angle in order to enhance viewing of the patient by the medical practitioner when positioned in front of the patient, as depicted in FIG. 1. Second portion 72 may be formed in a concave-convex shape to provide a magnifying effect to better enable the medical practitioner to view the portion of the patient upon which the procedure is to be performed.

Figure 6:
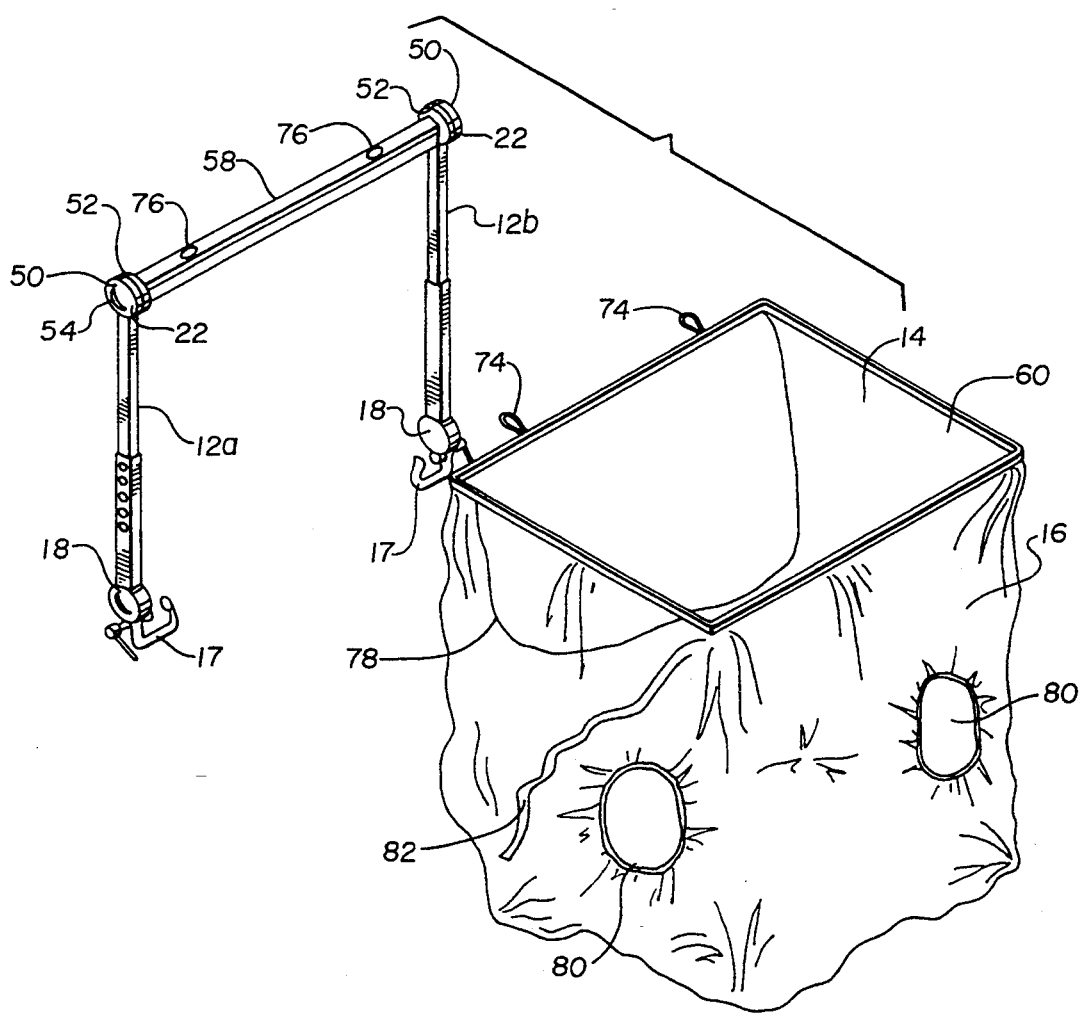
FIG. 6 is a perspective view of an embodiment of the invention depicting a clip-on viewer.

A further embodiment of transparent viewer 14 is shown in FIG. 6. A cross member 58 is utilized to connect frames 12a and 12b. The first end of cross member 58 is affixed to sleeve 52 of second rotatable joint 22 on frame 12a. The second end of cross member 58 is affixed to sleeve 52 of second rotatable joint 22 on frame 12b. In this embodiment, transparent viewer 14 has bayonet fittings 74 on the edge that will be closest to the patient. Bayonet fittings 74 are designed to be received within fitting receivers 76 shown in phantom in cross member 58. Bayonet fittings 74 are designed to support transparent viewer 14 in an extended position with respect to cross member 58.

FIG. 6 also illustrates viewer 14 with receptacle 16 adhered to viewer 14. In this embodiment, the viewer 14 and attached receptacle 16 are slid into channels 56 of frames 12a, 12b and supported therein. Braces 77 assist in providing structural support. Braces 77 may be varied in length by sliding first portion 81 within second portion 83 and affixing in the desired position by aligning bores 85 therethrough and affixing in a conventional manner with a nut and bolt or a pin. Varying the length of braces 77 permits the angle of viewer 14 to be varied with respect to frame 12. This embodiment permits the viewer 14 and receptacle 16 to be removed from frame 12 as a unit after the medical procedure is performed. Receptacle 16 may then be stripped from viewer 14 and disposed of and viewer may be cleaned.

Returning to FIGS. 1 and 2, receptacle 16 depends from and is supported by transparent viewer 14 by a conveniently removable means such as hook and pile fasteners or an adhesive that is applied to the rim of the opening of receptacle 16 and is pressure sensitive. A pressure sensitive adhesive may be made in two layers. The first layer is applied to the receptacle 16. The second layer is applied over the first layer. A removable wrapper is applied to the exposed surface of the second layer of adhesive. The wrapper permits handling of the receptacle 16 by an individual without receptacle 16 adhering to the hands of the individual. When the receptacle 16 is ready for application to the edge of viewer 14, the wrapper is removed by pulling an end of the wrapper. Since the first layer of adhesive forms a stronger bond to the receptacle 16 than the second layer of adhesive forms to the wrapper, the wrapper can be pulled away, leaving substantially all of the first layer of adhesive on the receptacle 16. Receptacle 16 can then be adhesively bonded to the rim of viewer 14.

In removal, the receptacle 16 is stripped from the lip of viewer 14. In this case, the first layer of adhesive has formed a stronger bond with the receptacle 16 than the viewer 14. Substantially all the adhesive is removed attached to the receptacle 16 as receptacle 16 is stripped from viewer 14. The remaining adhesive on the rim of receptacle 16 can the be brought into contact to substantially seal the opening of receptacle 16 In an alternative embodiment, the lip of the opening of receptacle 16 is removably attached to and stripped from the to frame member 20 in a manner similar to that previously described.

Receptacle 16 is bag shaped, and is formed of thin, pliable, transparent film. Receptacle 16 is deep enough to comfortably enclose the portion of the patient upon which the medical procedure is to be performed.

Figure 8:
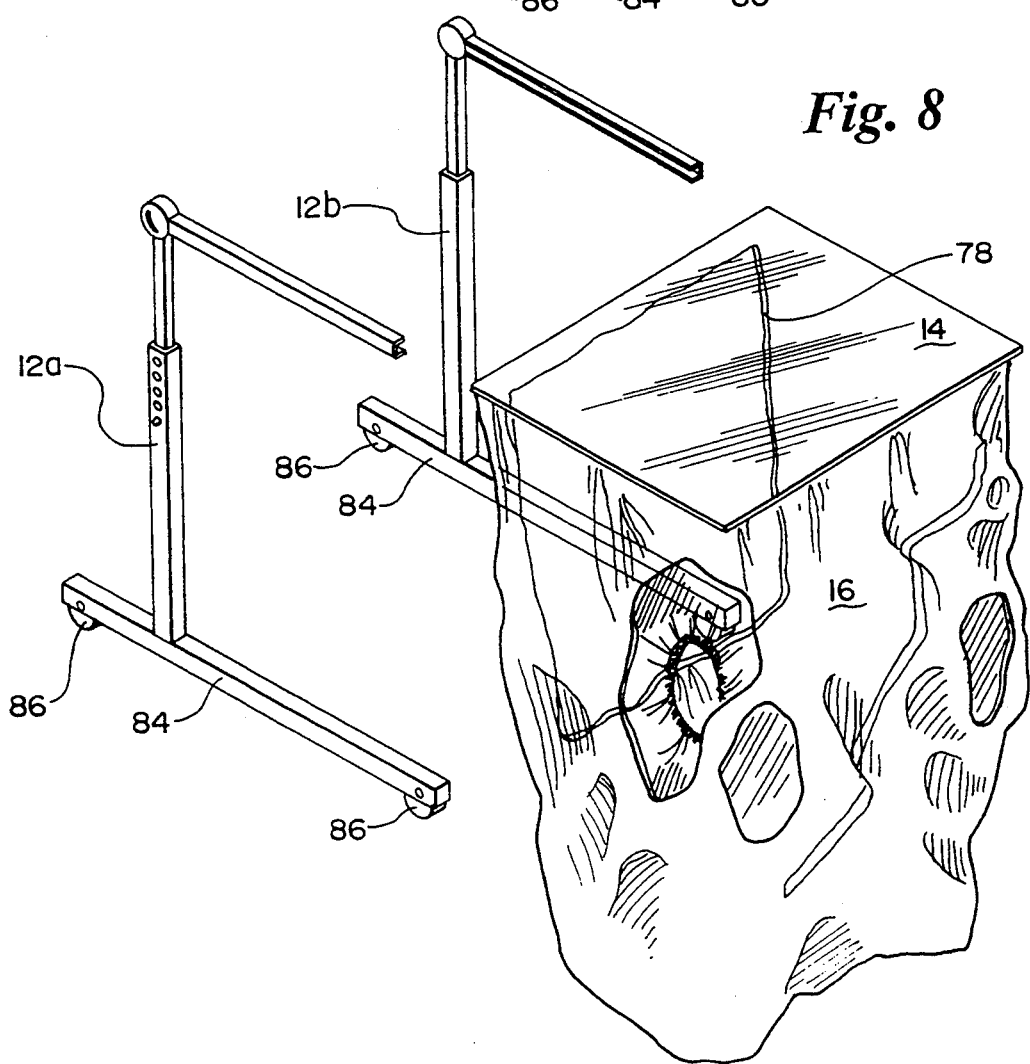
FIG. 8 is a perspective view of the free-standing embodiment showing the receptacle and viewing portion apart from the frame.

Patient opening 78 is shown in the rear wall of receptacle 16 in FIGS. 6, 8, and 10. In the embodiment shown in FIG. 8 and 10, patient opening 78 is a single opening large enough to receive, for example, both lower legs of a patient. Alternatively, a singular elasticized round opening 78 or, as depicted in FIG. 6, two elasticized round openings 78 may be provided. Such openings 78 may be rimmed with adhesives or elasticized in order to closely adhere to the legs of the patient. This allows the patient's foot freedom to be worked on by medical practitioners, but helps ensure that debris formed in the medical procedure is retained within the confines of receptacle 16.

Elasticized openings 80 are provided in receptacle 16 into which the medical practitioner may insert his or her hands as necessary to perform the procedure on the patient. In an alternative embodiment, flap 82 is provided. Flap 82 is an elongated opening with an adhesive provided on at least one edge. Such adhesive is of the type that will withstand repeated openings and reclosings and still provide adequate sealing of the opening. Flap 82 may be provided alternatively in either side or the front panel of receptacle 16.

Figure 7:
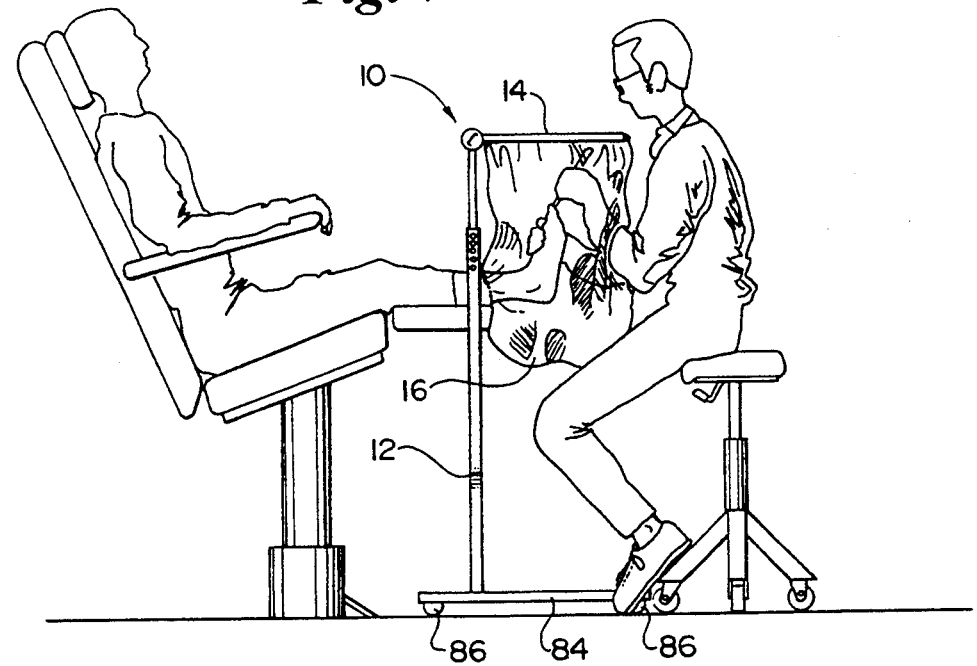
FIG. 7 is a side perspective of an alternative, free-standing embodiment of the present invention.

FIGS. 7 and 8 depict a free standing embodiment of the invention. Frame 12 is supported on legs 84. Legs 84 project a substantial distance under viewer 14 to provide the necessary balance to counter the cantilevered weight of viewer 14 and receptacle 16. Legs 84 each include a pair of wheels 86 to facilitate positioning the containment device 10 proximate the patient.

Referring to FIG. 9, an embodiment of the present invention is depicted in which viewer 14 is supported by and retained within viewer frame 90. Viewer frame 90 is generally rectangular shaped and formed of a metallic material. Viewer frame 90 is hinged by hinges 92 affixed in conventional manner to cross member 58. FIG. 9 depicts viewer frame 90 in the open, raised position in the solid lines and in the lowered, closed position in the phantom lines. In the open position, both sides of viewer 14 may be readily cleaned to ensure an antiseptic environment for the performance of successive medical procedures. The viewer frame 90 is held in the closed position during the medical procedures. In this embodiment, the receptacle 16 is removably adhered to the frame 90 by the means previously mentioned and depends therefrom to enclose the extremity of the patient. This embodiment may alternatively be utilized with the free standing frame 12 as depicted in FIGS. 7 and 8.

FIG. 10 depicts a further alternative embodiment of containment device 10. In this embodiment, viewer frame 90 is hinged by hinges 92 affixed in conventional manner to cross member 58 as depicted in FIG. 9. Additionally, viewer 14 is detachably installed in viewer frame 90 by utilizing bayonet fittings 74, as previously discussed in conjunction with FIG. 6. In this embodiment, the cleaning of viewer 14 is facilitated either by raising viewer 14 on hinges 92 or by removal of viewer 14 from viewer frame 90. In this embodiment, receptacle 16 may be removably adhered to either viewer frame or to viewer 14 as has been previously described. This embodiment may alternatively be utilized with the free standing frame 12 as depicted in FIGS. 7 and 8.

In operation, patient, depicted at 6, is supported on a chair or on a bedside. The medical practitioner, shown at 8, is seated proximate the portion of the patient upon which the medical procedure is to be performed. Containment device 10 is erected by positioning clamp 17 on the frame of the bed or chair upon which the patient is supported. The rotatable connection between clamp 17 and first rotatable joint 18 permits clamp 17 to be oriented to accommodate the various positions of the frame of the chair or bed. Turning down on handle 32 of clamp 17 firmly engages frame 12 to the frame. Alternatively, the free standing frame 12 as depicted in FIGS. 7 and 8 is positioned proximate the patient and the medical practitioner is seated opposite the patient.

Once containment device 10 is suitably positioned relative to the patient, the position of first frame member 20 may be set. This is accomplished by loosening butterfly nut 40 of first rotatable joint 18. The angle of first frame member 20 with respect to clamp 17 may then be freely adjusted. When first frame member 20 is in the position desired, butterfly nut 40 is again tightened, thereby fixing the position of first frame member 20.

The height of frame 12 is adjusted by withdrawing locking pin 48. Second telescoping member 44 may then be either extended or retracted with respect to first telescoping member 42. When the desired height is achieved, the bore in second telescoping member 44 is visually aligned with the nearest bore 46 in first telescoping member 42, and locking pin 48 is reinserted.

The angular relationship of first frame member 20 and second frame member 24 is adjusted by second rotatable joint 22 in a manner that is similar to the description of the adjustment of first rotatable joint 18.

The embodiment shown in FIG. 2 is assembled by adjusting the lateral dimension of receptacle 16 by sliding first slidable portion 64 and second slidable portion 66 of transparent viewer 14 with respect to one another. When the lateral dimension of viewer 14 approximates the distance between second frame member 24 of frame 12a and second frame member 24 of frame 12b, the lateral edges 68 of transparent viewer 14 are slideably engaged with channel 56 of second frame members 24.

In the embodiment shown in FIG. 6, the angular relationship of transparent viewer 14 with respect to the first frame members 20, is adjusted by utilizing the second rotatable joint 22 both frames 12a, 12b. This is accomplished by rotating cross member 58. By setting butterfly nuts 54 on second rotatable joints 22, cross member 58 is held in the desired angular relationship with respect to first frame members 20. In this embodiment, receptacle 16 is set in place by sliding bayonet fittings 74 into fitting receivers 76.

The debris that is generated from the medical procedure is captured in the receptacle 16 and contained therein. Receptacle 16 is designed to retain debris that may be describe as comprising toenail dust, bone dust, clippings, and skin particles. Receptacle 16 is not designed to contain aerosols and the like that require a greater degree of integrity than is incorporated herein. The present invention is designed primarily for in-office treatment with procedures that do not generate such aerosol contaminants.

At the completion of the medical procedure, the receptacle 16 is removed from the viewer 14 or from frame member 20 and is slipped off the patient's extremity. The debris is retained within the receptacle 16 and the entire receptacle is then properly disposed of. The viewer 14 is then cleaned prior to use with a subsequent patient. In the embodiments shown in FIGS. 9 and 10, the cleaning is facilitated by hinging the viewer 14 or by removal of the viewer 14 from the frame 12. A new receptacle 16 may then be adhered to viewer 14 or to the viewer frame 90 and a subsequent patient may then be examined and treated in a clean environment.

It is understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

I claim:

1. A containment device for use by a medical practitioner during medical procedures on a portion of a patient to contain debris generated thereby, comprising:
    a supporting frame having at least one upright stanchion and at least one cantilevered arm operably coupled to the upright stanchion proximate a first end thereof;
    a receptacle frame operably coupled to and supported by the cantilevered arm;
    a transparent viewing member supported by said receptacle frame; and
    a transparent, disposable receptacle operably removably coupled to and depending from the receptacle frame, defining an interior space and having structure defining at least one aperture therein designed to admit a portion of a patient to the interior space and having structure defining a plurality of apertures therein to facilitate admission of medical instruments and a medical practitioners hands to said interior space, wherein the viewing member and the receptacle act cooperatively to substantially enclose the portion of the patient and to retain therein substantially all of the debris generated during a medical procedure performed therein.

2. A containment device as claimed in claim 1 further including the receptacle frame having selectably angularly variable coupling with the supporting frame, said coupling designed to selectively adjust the angle of the transparent viewing member as desired.

3. The containment device as claimed in claim 1 wherein the receptacle further includes a pressure sensitive adhesive imposed on a portion thereof and being designed to engage the receptacle frame and to be readily disengaged therefrom to facilitate the ready disposal of the receptacle and the debris contained therein.

4. A containment device as claimed in claim 1 further including the aperture defined in the receptacle to admit a portion of the patient therethrough having sealing means disposed proximate the structure defining said aperture for sealingly engaging the portion of the patient and for resealing said aperture upon removal of the portion of the patient therefrom.

5. A containment device as claimed in claim 1 further including the plurality of apertures defined in the receptacle to facilitate admission of medical instruments and a medical practitioner's hands to said interior space having sealing means disposed proximate the structure defining said apertures for sealingly engaging the medical instruments and a medical practitioner's hands and for resealing said apertures upon removal of the medical instruments and a medical practitioner's hands therefrom.

6. A containment device as claimed in claim 1 further including floor engaging rollers operably coupled to said supporting frame proximate a second end thereof to facilitate the ready positioning of the containment device.

7. A containment device as claimed in claim 1 further including at least one clamp member operably coupled to said supporting frame proximate a second end thereof to facilitate the ready clamping of the containment device to a structure.

* * * * *

UNITED STATES PATENT AND TRADEMARK OFFICE
CERTIFICATE OF CORRECTION

PATENT NO. : 5,396,904
DATED : March 14, 1995
INVENTOR(S) : William J. Hartigan, Jr.

It is certified that error appears in the above-indentified patent and that said Letters Patent is hereby corrected as shown below:

Col. 2, line 28, delete "to" after the word -- tissue --;

Col. 2, line 39, insert "to" after the word -- adhere --;

Col. 3, line 11, delete "practitioner" and insert -- practitioners --;

Col. 6, line 5, delete "attached to" and insert -- from --;

Col. 6, line 7, delete "the" and insert -- then --;

Col. 6, line 8, insert " . " after 16;

Col. 6, line 10, delete "to", second occurrence;

Col. 7, line 8, insert "90" after the word -- frame --;

Col. 7, line 67, delete "describe" and insert -- described --;

Col. 8, line 45, delete "practitioners" and insert -- practitioner's --;

Col. 8, line 45, begin a new paragraph with the word "wherein".

Signed and Sealed this

Ninth Day of January, 1996

Attest:

BRUCE LEHMAN

*Attesting Officer*     *Commissioner of Patents and Trademarks*